United States Patent [19]

Morita

[11] Patent Number: 4,808,577

[45] Date of Patent: Feb. 28, 1989

[54] METHOD FOR PREVENTING COLORATION OF AQUEOUS PREPARATIONS OF CEFMENOXIME

[75] Inventor: Yasushi Morita, Takasaki, Japan

[73] Assignee: Senju Pharmaceutical Co., Ltd., Osaka, Japan

[21] Appl. No.: 61,377

[22] Filed: Jun. 15, 1987

[30] Foreign Application Priority Data

Jun. 26, 1986 [JP] Japan .................................. 61-150085

[51] Int. Cl.$^4$ .................... A61K 31/69; A61K 31/545
[52] U.S. Cl. ...................................... 514/64; 514/201; 514/912
[58] Field of Search ......................... 514/64, 201, 912

[56] References Cited

U.S. PATENT DOCUMENTS 4,098,888  7/1978  Ochiai et al. ........................ 514/201
4,551,456  11/1985  Katz ..................................... 514/912

OTHER PUBLICATIONS

The Merck Index, Tenth Edition, p. 269 (1983).

*Primary Examiner*—Jerome D. Goldberg
*Attorney, Agent, or Firm*—Armstrong, Nikaido, Marmelstein & Kubovcik

[57] ABSTRACT

Incorporation of boric acid or a salt thereof in an aqueous preparation containing cefmenoxime or a salt thereof is effective in the prevention of coloration of the preparation.

Therefore, cefmenoxime and its salts can be used as aqueous ophthalmic, otic or nasal drugs for topical application.

9 Claims, No Drawings

METHOD FOR PREVENTING COLORATION OF AQUEOUS PREPARATIONS OF CEFMENOXIME

BACKGROUND OF THE INVENTION

The present invention relates to a method for preventing coloration of cefmenoxime or a salt thereof (hereinafter referred to as subject compound) in an aqueous solution or suspension.

Cefmenoxime hemi-hydrochloride, which is a representative subject compound of the present invention, has the following structural formula:

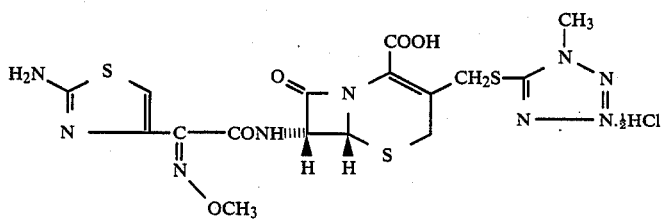

The subject compound of the present invention has a broad antibacterial spectrum encompassing gram-positive and gram-negative aerobic and anaerobic bacteria, is stable against various $\beta$-lactamases, and displays high antibacterial activity against $\beta$-lactamase producing strains. In view of these properties of the subject compound, there is a standing demand for topical preparations of the subject compound which may be used in ophthalmological, otological and rhinological fields.

When an aqueous solution of the subject compound is allowed to stand, it is markedly colorized quickly and it is the state of the art that in the absence of an effective means for preventing this coloration, there is no clinically useful liquid preparation of the subject compound.

It has thus been difficult to produce an aqueous preparation that is stable enough to permit administration as ear-drops, eye-drops or nasal drops.

Under the circumstances, the present inventor sought for a way of preventing coloration of liquid preparations of the subject compound for the purpose of developing stable aqueous preparations of the subject compound. First, a large number of compounds which have been commonly used as stabilizers or coloration inhibitors for various unstable drugs were explored for their utility in the prevention of coloration of cefmenoxime in aqueous solution. It was, however, found that they were either not effective at all in the prevention of coloration of cefmenoxime or rather tended to accelerate the coloration.

SUMMARY OF THE INVENTION

The present inventors found surprisingly that the addition of boric acid or a salt thereof to an aqueous solution of cefmenoxime, the coloration of the solution was markedly inhibited. The present invention is predicated on the above finding.

The present invention is therefore directed to a method for preventing coloration of aqueous preparations of the subject compound which comprises incorporating boric acid or a salt thereof in an effective amount in an aqueous preparation of the subject compound.

DETAILED DESCRIPTION OF THE INVENTION

The method according to the present invention is of value in the application of cefmenoxime or a salt thereof as ophthalmic, otic or nasal preparations for topical use.

As the above-mentioned salt of cefmenoxime, there may be used inorganic salts such as hydrochloride, sulfate, etc. and organic acid salts such as acetate, citrate and so on. Particularly preferred is the hydrochloride.

As the salt of boric acid, borax may be mentioned as an example.

In accordance with the present invention, boric acid or a salt thereof is used generally in a proportion of 0.01 to 20 weight parts to each weight part of the subject compound, preferably in the range of 0.05 to 8 weight parts, and for still better results, in the range of 0.1 to 4 weight parts.

The concentration of the subject compound in aqueous medium, for which the addition of boric acid or a salt thereof according to the invention may prove effective in the prevention of coloration, is in the range of 0.01 to 10 w/v %, preferably in the range of 0.05 to 5 w/v %, and for still better results, in the range of 0.1 to 2 w/v %.

The level of addition of boric acid or a salt thereof is generally in the range of 0.01 to 5 w/v %, preferably 0.05 to 3 w/v %, and for still better results, 0.1 to 2 w/v %.

The pH of the aqueous preparation provided in accordance with the present invention may range from pH about 4 to pH about 8 but in consideration of the stability of the subject compound, it is preferably in the range of pH about 5 to pH about 7.

Unless contrary to the object of the invention, the aqueous preparation according to the invention may further contain various additives which are generally used in aqueous pharmaceutical products, such as buffers for pH adjustment (phosphate buffer, boric acid buffer, citric acid buffer, tartaric acid buffer, acetic acid buffer, etc.), isotonizing agents (sorbitol, glycerol, polyethylene glycol, propylene glycol, glucose, sodium chloride, etc.), antiseptics (benzalkonium chloride, p-hydroxybenzoates, benzyl alcohol, p-chloromethoxyphenol, chlorocresol, phenethyl alcohol, sorbic acid and its salts, thimerosal, chlorobutanol, etc.), chelating agents (sodium edetate, sodium citrate, sodium polyphosphate, etc.), and rheology modifiers (polyvinylpyrrolidone, methylcellulose, carboxymethylcellulose sodium, hydroxypropylcellulose, polyvinyl alcohol, sodium polyacrylate, etc.) in the concentrations generally employed. These additives may be previously added to an aqueous solution or suspension of the subject compound or may be provided in admixture with boric acid or a salt thereof. It may also be possible to first dissolve these additives and boric acid or a salt thereof in aqueous medium and, then, dissolve the subject compound in the solution. All that is essential is that boric acid or a salt thereof is ultimately present in the final aqueous preparation of the subject compound.

Unless contrary to the object of the present invention, any medicinally active substance in addition to the subject compound may be incorporated in the aqueous preparation according to the present invention.

Thus, in accordance with the present invention, the coloration of cefmenoxime and its salts in aqueous media can be remarkably suppressed by incorporation of boric acid or a salt thereof.

Therefore, cefmenoxime and its salts can now be used as ophthalmic, otic and nasal drugs for topical application.

EXAMPLES

The following experimental and formulation examples are further illustrative of the present invention.

EXPERIMENTAL EXAMPLE 1

Stability Test

For the purpose of demonstrating the coloration-inhibitory effect of boric acid on an aqueous solution of cefmenoxime hydrochloride, a comparative stability test was conducted using boric acid and, as controls, various coloration inhibitors or stabilizers. The coloration inhibitors or stabilizers used as controls were sodium phosphate, sodium acetate, lysine, glycerol, trisodium citrate, taurin, sodium thiosulfate, sodium L-glutamate, sodium edetate, nicotinamide, and methionine.

Aqueous preparations (pH 7) containing 1.0 w/v % of cefmenoxime hydrochloride, 0.24 w/v % of sodium carbonate as solubilizer, and 0.1 w/v % of one of said coloration inhibitors or stabilizers were allowed to stand at 15° C. for 7 days and the degrees of coloration of the preparations were evaluated. As shown in Table 1, the preparations containing coloration inhibitors or stabilizers other than boric acid were markedly colored. The evaluation of color was made by a panel of 5 assessors according to the following scoring scheme based on Bureau of Pharmaceutical Affairs, Japanese Ministry of Health and Welfare Bulletin No. 338 of Apr. 1, 1981, Notification 35-37. The results are shown in Table 1.

| Color | Score |
|---|---|
| Colorless | 0 |
| Pale yellow | 1 |
| Light yellow | 2 |
| Yellow | 3 |
| Deep yellow | 4 |
| Orange yellow | 5 |
| Orange | 6 |

The higher the score is, the higher is the intensity of color.

TABLE 1

| Coloration inhibitor or stabilizer | Panelist A | B | C | D | E | Mean score |
|---|---|---|---|---|---|---|
| Boric acid | 0 | 0 | 0 | 1 | 0 | 0.2 |
| Sodium phosphate | 5 | 5 | 5 | 5 | 5 | 5.0 |
| Sodium acetate | 5 | 5 | 5 | 5 | 5 | 5.0 |
| Trisodium citrate | 6 | 5 | 6 | 6 | 6 | 5.8 |
| Sodium edetate | 6 | 6 | 5 | 6 | 6 | 5.8 |
| Sodium L-glutamate | 6 | 6 | 6 | 6 | 6 | 6.0 |
| Lysine | 5 | 5 | 5 | 5 | 5 | 5.0 |
| Taurin | 6 | 6 | 5 | 6 | 6 | 5.8 |
| Nicotinamide | 6 | 6 | 6 | 6 | 6 | 6.0 |

TABLE 1-continued

| Coloration inhibitor or stabilizer | Panelist A | B | C | D | E | Mean score |
|---|---|---|---|---|---|---|
| Glycerol | 5 | 5 | 5 | 5 | 5 | 5.0 |
| Sodium thiosulfate | 6 | 5 | 6 | 6 | 6 | 5.8 |
| Methionine | 6 | 6 | 6 | 6 | 6 | 6.0 |
| Negative control | 5 | 5 | 6 | 5 | 5 | 5.2 |

EXPERIMENTAL EXAMPLE 2

The coloration-inhibitory effect of boric acid was further investigated by using cefmenoxime hydrochloride at a concentration of 1.0 w/v % and varying the concentration of boric acid. The pH of preparations was set at pH 7. Using the formulations shown in Table 2, test preparations were prepared and allowed to stand at 15° C. for 7 days and the degrees of coloration were investigated. The results are shown in Table 3.

TABLE 2

| | Formulation | | | | | | | |
|---|---|---|---|---|---|---|---|---|
| | 1 | 2 | 3 | 4 | 5 | 6 | 7 | 8 |
| Boric acid (w/v %) | 1.8 | 0.9 | 0.45 | 0.2 | 0.1 | 0.05 | 0.01 | — |
| Sodium carbonate (w/v %) | 0.24 | 0.24 | 0.24 | 0.24 | 0.24 | 0.24 | 0.24 | 0.24 |

TABLE 3

| | Panelist A | B | C | D | E | Mean score |
|---|---|---|---|---|---|---|
| Formulation 1 | 0 | 0 | 0 | 1 | 0 | 0.2 |
| Formulation 2 | 1 | 0 | 0 | 0 | 0 | 0.2 |
| Formulation 3 | 0 | 0 | 0 | 0 | 1 | 0.2 |
| Formulation 4 | 0 | 0 | 0 | 1 | 0 | 0.2 |
| Formulation 5 | 0 | 1 | 0 | 0 | 0 | 0.2 |
| Formulation 6 | 2 | 2 | 2 | 3 | 2 | 2.2 |
| Formulation 7 | 5 | 5 | 6 | 6 | 5 | 5.4 |
| Formulation 8 | 6 | 5 | 6 | 6 | 6 | 5.8 |

It is apparent from the above results that the coloration-inhibitory effect of boric acid begins to appear at the concentration of 0.01 w/v % and is overt at 0.05 w/v % and remarkable at 0.1 w/v % and higher concentrations.

EXPERIMENTAL EXAMPLE 3

The coloration-inhibitory effect of boric acid was further investigated by using cefmenoxime hydrochloride at a concentration of 1.0 w/v and varying the pH as shown in Table 4. In this experiment, too, test preparations were allowed to stand at 15° C. for 7 days and the degrees of coloration were investigated. The results are shown in Table 5.

TABLE 4

| | Formulation | | |
|---|---|---|---|
| | 9 | 10 | 11 |
| Boric acid (w/v %) | 0.1 | 0.1 | 0.1 |
| Sodium carbonate (w/v %) | 0.24 | 0.24 | 0.24 |
| pH* | 5.5 | 6.5 | 7.5 |

TABLE 5

| | Panelist A | B | C | D | E | Mean score |
|---|---|---|---|---|---|---|
| Formulation 9 | 0 | 0 | 1 | 0 | 0 | 0.2 |
| Formulation 10 | 1 | 0 | 0 | 0 | 0 | 0.2 |

TABLE 5-continued

| | Panelist | | | | | |
|---|---|---|---|---|---|---|
| | A | B | C | D | E | Mean score |
| Formulation 11 | 3 | 2 | 3 | 2 | 2 | 2.4 |

It is apparent from the above results that the coloration-inhibitory effect of boric acid was the most pronounced at pH about 5 to 7. At pHs less than 4 or in excess of 8, the subject compound is too unstable to be practically useful.

The formulation examples given below are further illustrative of the present invention.

FORMULATION EXAMPLE 1

(Otic Preparation)

| Cefmenoxime hemi-hydrochloride | 1.0 g |
|---|---|
| Sodium carbonate | 0.24 g |
| Boric acid | 0.1 g |
| Sodium chloride | 0.5 g |
| Methyl p-hydroxybenzoate | 0.02 g |
| Sodium hydroxide | q.s. (pH 6.0) |
| Sterile pure water | To make 100 ml |

In about 80 ml of warmed sterile pure water is dissolved 0.02 g of methyl p-hydroxybenzoate and after the solution is cooled to room temperature, 0.1 g of boric acid, 0.24 g of sodium carbonate, 0.5 g of sodium chloride and 1.0 g of cefmenoxime hemi-hydrochloride are successively added and dissolved. Then, the solution is adjusted to pH about 6.0 with sodium hydroxide, followed by addition of sterile pure water to make 100 ml. This solution is sterilized by filtration (0.45 μm) and aseptically filled into plastic dropper bottles for otic use.

FORMULATION EXAMPLE 2

(Ophthalmic Preparation)

| Cefmenoxime hemi-hydrochloride | 0.5 g |
|---|---|
| Borax | 0.9 g |
| Sodium dihydrogen phosphate | 0.8 g |
| Sodium chloride | 0.2 g |
| Chlorobutanol | 0.2 g |
| Sodium hydroxide | q.s. (pH 7.0) |
| Sterile pure water | To make 100 ml |

In about 80 ml of sterile pure water are successively dissolved 0.5 g of cefmenoxime hemi-hydrochloride, 0.9 g of borax, 0.8 g of sodium dihydrogen phosphate, 0.2 g of sodium chloride and 0.2 g of chlorobutanol. The solution is adjusted to pH 7.0 with sodium hydroxide and a further amount of sterile pure water is added to make 100 ml. This solution is sterilized by filtration (0.45 μm) and aseptically filled into plastic applicator-bottles for ophthalmic use.

FORMULATION EXAMPLE 3

(Ophthalmic Preparation)

In 100 ml of pure water are dissolved 0.8 g of boric acid, 0.7 g of borax, 0.1 g of sodium chloride and 0.04 g of butyl p-hydroxybenzoate. To this solution is added a tablet containing 1.2 g of cefmenoxime as an active ingredient, which is dissolved by thorough stirring to give an ophthalmic solution.

FORMULATION EXAMPLE 4

(Ophthalmic Preparation)

A powder containing 0.5 g of cefmenoxime, 0.1 g of sodium carbonate and 0.6 g of sodium chloride is added to a solution of 1.2 g of boric acid, 0.2 g of disodium phosphate and 0.02 g of sodium edetate in 100 ml of sterile pure water, followed by thorough stirring to give an ophthalmic preparation.

What is claimed is:

1. An aqueous cefmenoxime composition inhibited against discoloration comprising 0.01 to 20 parts of boric acid or a salt thereof per part by weight of cefmenoxime or a salt thereof, wherein the concentration of cefmenoxime or a salt thereof is in the range of 0.01 to 10% (w/v), and the concentration of the boric acid or a salt thereof is in the range of 0.01 to 5% (w/v).

2. A composition according to claim 1 containing 0.05 to 8 parts by weight of the boric acid or a salt thereof per part of the cefmenoxime or a salt thereof.

3. A composition according to claim 2 containing 0.1 to 4 parts of the boric acid or a salt thereof per part by weight of the cefmenoxime or a salt thereof.

4. A composition according to claim 1 containing 0.05 to 5% (w/v) of cefmenoxime or a salt thereof.

5. A composition according to claim 4 containing 0.1 to 2% (w/v) of cefmenoxime or a salt thereof.

6. A composition according to claim 1 having a pH of 4-8.

7. A composition according to claim 6 having a pH of 5-7.

8. A composition according to claim 1 formulated for ophthalmic use.

9. A composition according to claim 1 formulated for otic use.

* * * * *